United States Patent [19]
Fisher et al.

[11] Patent Number: 5,504,229
[45] Date of Patent: Apr. 2, 1996

[54] SYNTHESIS OF ALIPHATIC $C_2$-$C_{22}$ CARBOXYLIC ACIDS

[75] Inventors: Karl Fisher, Hohen-Suelzen; Gerhard Fritz, Dannstadt-Schauernheim, both of Germany

[73] Assignee: BASF Aktiengesellschaft, Ludwigshafen, Germany

[21] Appl. No.: 285,158

[22] Filed: Aug. 3, 1994

[30] Foreign Application Priority Data

Aug. 10, 1993 [DE] Germany .................. 43 26 775.0

[51] Int. Cl.⁶ .................................................. C07D 51/16
[52] U.S. Cl. ............................................................ 554/134
[58] Field of Search .................................... 554/134

[56] References Cited

FOREIGN PATENT DOCUMENTS 0239237 1/1987 Czechoslovakia .

OTHER PUBLICATIONS

Chemical Abstract, JP 78/104,413, 1978.

*Primary Examiner*—José G. Dees
*Assistant Examiner*—Deborah D. Carr
*Attorney, Agent, or Firm*—Keil & Weinkauf

[57] ABSTRACT

Synthesis of aliphatic $C_2$-$C_{22}$ carboxylic acids by oxidation of relevant aldehydes with oxygen in the presence of alkali metal compounds or alkaline earth metal compounds in the liquid phase and separation of the reaction mixture by distillation, in which the bottom product formed during distillation and containing an alkali metal salt or alkaline earth metal salt is recycled to the oxidation stage.

4 Claims, No Drawings

SYNTHESIS OF ALIPHATIC $C_2$-$C_{22}$ CARBOXYLIC ACIDS

The present invention relates to an improved process for the preparation of aliphatic $C_2$–$C_{22}$ carboxylic acids by oxidation of relevant aldehydes with oxygen in the presence of alkali metal compounds or alkaline earth metal compounds in the liquid phase and fractional distillation of the reaction mixture.

It is known to be possible to prepare aliphatic carboxylic acids by oxidation of relevant aldehydes with oxygen. This process can be advantageously carried out in the presence of basic alkali metal compounds or alkaline earth metal compounds such as hydroxides, carbonates, acetates and oxides of lithium and alkaline earth metals (JP-A 78/105,41 3). CS-A 239,237 teaches furthermore the oxidation of 2-ethylhexanal in the presence of the sodium salt of 2-ethylhexanoic acid. In these reactions by-products having higher or lower boiling points are formed in addition to the target product, ie, for example, aldol condensates of the aldehyde used as well as oxidized aldol condensates.

In a conventional industrial purifying plant, the reaction mixture is fractionated into low-boiling components, the carboxylic acid, and a bottom product, which mainly consists of alkali metal salts or alkaline earth metal salts of the relevant carboxylic acid and high-boiling fractions. This bottom product is admixed with an acid to neutralize the carboxylates, and the carboxylic acid thus liberated is recycled to the distillation stage. The metal salt formed as a result of neutralization is removed from the system. This process suffers from the drawback that it is necessary to replenish the system with an alkali metal salt or alkaline earth metal salt to make up for that removed.

It is an object of the present invention to provide a process which does not suffer from this drawback.

Accordingly, we have found a process for the preparation of an aliphatic $C_2$–$C_{22}$ carboxylic acid by oxidation of a relevant aldehyde with oxygen in the presence of an alkali metal salt or alkaline earth metal salt in the liquid phase and separation of the reaction mixture by distillation, wherein the bottom product formed during distillation and containing an alkali metal salt or alkaline earth metal salt is recycled to the oxidation stage.

According to the present invention use may be made of $C_2$–$C_{13}$ aldehydes such as pentadecanal, icosanal, docosanal, or mixtures of such compounds, which may be linear or branched, preferably $C_3$–$C_9$ aldehydes such as propionaldehyde, butyraldehyde, isobutyraldehyde, n-hexanal and isononanal, but especially 2-ethylhexanal.

These aldehydes are usually caused to react with oxygen in a molar ratio of aldehyde to oxygen of from 1:0.5 to 1.1. The reaction temperature is generally 20°–150° C., in particular 30°–60° C. Generally speaking, the reaction is carried out at atmospheric pressure or pressures ranging up to 20 bar.

The reaction is carried out in the presence of alkali metal salts or alkaline earth metal salts, compounds soluble in the reaction mixture being particularly suitable. To the reaction mixture there are preferably added basic compounds such as hydroxides, oxides, acetates, carbonates and the salts of the carboxylic acids formed during respective oxidations. Sodium hydroxide and potassium hydroxide are particularly preferred. The reaction can be started using basic salts such as KOH, but is maintained thereafter by the recycled carboxylates. Generally speaking, amounts ranging from 0.1 to 10 wt %, and preferably from 0.2 to 2.5 wt%, of metal salt are used, based on the total batch.

The reaction may be carried out with or without a solvent. Particularly suitable solvents are aliphatic alcohols, aliphatic und aromatic hydrocarbons, ketones and esters, which can be present in amounts of from 0.1 to 50 wt%, based on the total batch.

The reaction is generally complete after 2 to 10h. It may be carried out continuously or batchwise.

The resulting reaction mixture is subjected to distillation, during which low-boiling components are separated and the aliphatic carboxylic acid is isolated. The bottoms resulting from distillation are recycled to the oxidation stage. This bottom product mainly consists of alkali metal salts or alkaline earth metal salts during the initial runs, but after repeated recycling, the precentage of high-boiling constituents therein rises.

The advantage of the process of the invention resides in the fact that no alkali metal salts or alkaline earth metal salts need to be subsequently introduced into the reactor. The removal of alkali metal salts or alkaline earth metal salts from the system is unnecessary.

Moreover, the process of the invention provides for a technically simple method of working up the material to provide the end products. It is to be noted that the product can be isolated in higher yield and purity than in a process not employing recycling.

The end products are desirable intermediates for the dyestuffs, pharaceuticals, and plastics industries, for example, for the manufacture of alkyd resins.

EXAMPLE

Preparation of 2-ethylhexanoic acid 12.82kg/h of 2-ethylhexanal and 1.79kg/h of oxygen (molar ratio 1:0.56) were caused to react in the presence of 1.9wt% of potassium 2-ethylhexanoate (prepared by the addition of KOH to the initial reaction mixture) at 40° C. and a pressure of 3 bar. 96 % of 2-ethylhexanoic acid having a color value of 4 were isolated by distillation (determined as specified in ISO 6271 ). The bottoms were recycled to the oxidation stage.

Comparative Example

An identical reaction mixture was purified by distillation as in the above example. The bottoms were acidified with nitric acid, washed and recycled to the distillation stage. The product thus isolated in a yield of 86 % had a color value of 8. Moreover potassium nitrate formed during the working up process had to be removed from the system.

We claim:

1. In a process for the preparation of an aliphatic $C_2$–$C_{22}$ carboxylic acid by oxidation of a relevant aldehyde with oxygen in the presence of an alkali metal salt or alkaline earth metal salt in the liquid phase and separation of the reaction mixture by distillation, the improvement which comprises: recycling the bottom product formed during distillation and containing an alkali metal salt or alkaline earth metal salt to the oxidation stage.

2. An process as defined in claim 1, wherein sodium hydroxide or potassium hydroxide is used as alkali metal compound.

3. An process as defined in claim 1, wherein 2-ethylhexanal is converted to 2-ethylhexanoic acid.

4. An process as defined in claim 2, wherein 2-ethylhexanal is converted to 2-ethylhexanoic acid.

* * * * *

UNITED STATES PATENT AND TRADEMARK OFFICE
CERTIFICATE OF CORRECTION

PATENT NO.: 5,504,229

DATED: April 2, 1996

INVENTOR(S): FISCHER et al.

It is certified that error appears in the above-identified patent and that said Letters Patent is hereby corrected as shown below:

After "An" insert --improved-- at the following places:

Column 2, claim 2, line 59;

claim 3, line 62; and claim 4, line 64.

Signed and Sealed this

Fifth Day of November, 1996

Attest:

BRUCE LEHMAN

*Attesting Officer*     *Commissioner of Patents and Trademarks*